United States Patent [19]

Bagli et al.

[11] Patent Number: 4,469,694

[45] Date of Patent: Sep. 4, 1984

[54] 2-(1-PIPERAZINYL)-2,4,6-CYCLOHEPTATRIEN-1-ONE DERIVATIVES

[75] Inventors: Jehan F. Bagli, Kirkland; Tibor Bögri, Montreal; Katherine Voith, Dorval, all of Canada

[73] Assignee: Ayerst, McKenna & Harrison Inc., Montreal, Canada

[21] Appl. No.: 124,164

[22] Filed: Feb. 25, 1980

[51] Int. Cl.$^3$ .................. A61K 31/495; C07D 241/04
[52] U.S. Cl. .................................... 424/250; 544/358; 544/368; 544/369; 544/370; 544/373; 544/376; 544/392; 544/399
[58] Field of Search ................ 424/250; 544/368–369, 544/370, 376, 373, 389, 392, 358; 542/429

[56] References Cited

PUBLICATIONS

Sianesi, et al., "J. Med. Chem.", vol. 10, 1967, pp. 1144–1148.
Biggi, et al., "J. Amer. Chem. Soc.", vol. 94, 1972, pp. 4700–4707, vol. 95, 1973, pp. 7101–7107.
Toda, et al., "Chemical Abstracts", vol. 76, 1972, col. 72185f.
Veracini, et al., "J. Chem. Soc. Commun.", 1977, pp. 623–624.
Abadir, et al., "J. Chem. Soc.", 1952, pp. 2350–2353.
Nozoe, et al., "Chemical Abstracts", vol. 70, 1969, col. 87244z.

*Primary Examiner*—Donald G. Daus
*Assistant Examiner*—James H. Turnipseed
*Attorney, Agent, or Firm*—Arthur E. Wilfond

[57] ABSTRACT

2-(1-Piperazinyl)-2,4,6-cycloheptatrien-1-one derivatives, therapeutically acceptable acid addition salts thereof, processes for their preparation, methods of using the derivatives and pharmaceutical compositions of the derivatives are disclosed. The derivatives exhibit dopamine-receptor stimulating activity in a mammal and are useful for treating hyperprolactinemia, galactorrhea, amenorrhea, impotence, Parkinsonism, diabetes, acromegaly, hypertension and other central nervous system disorders.

35 Claims, No Drawings

2-(1-PIPERAZINYL)-2,4,6-CYCLOHEPTATRIEN-1-ONE DERIVATIVES

BACKGROUND OF THE INVENTION

This invention relates to novel 2-(1-piperazinyl)-2,4,6-cycloheptatrien-1-one derivatives, to therapeutically acceptable acid addition salts thereof, to a process for their preparation, to methods of using the derivatives and to pharmaceutical compositions of the derivatives. These derivatives exhibit dopamine-receptor stimulating activity in a mammal. Thus, they can be useful for treating hyperprolactinemia, galactorrhea, amenorrhea, impotence, Parkinsonism, diabetes, acromegaly, hypertension and other central nervous system disorders which respond to dopamine-receptor stimulation.

The following references were obtained from a literature search for 2-substituted tropones: E. Sianezi et al., J. Med. Chem., 10, 1144 (1967); G. Biggi et al., J. Amer. Chem. Soc., 94, 4700 (1972); T. Toda et al., Chem. Abstr., 76, 72185f (1972) for Bull. Chem. Soc. Jap., 45, 226 (1972); G. Biggi et al., J. Amer. Chem. Soc., 95, 7101 (1973); C. A. Veracini et al., J. Chem. Soc. Commun., 623 (1974); B. J. Abadir et al., J. Chem. Soc., 2350 (1952) and T. Nozoe et al., Chem. Abstr., 70, 87244z (1969) for Bull. Chem. Soc. Jap., 41, 2978 (1968). These references disclose compounds which like the compounds of this invention are 2,4,6-cycloheptatrien-1-one derivatives. Of these 2,4,6-cycloheptatrien-1-one derivatives, the 2-piperidinyl-2,4,6-cycloheptatrien-1-one described by G. Biggi et al., J. Amer. Chem. Soc., 94, 4700 (1972), cited above, can be considered the most closely related to the compounds of this invention. However, the latter 2-piperidinyl derivative is treated as a chemical curiosity without any indicated useful pharmacological activity. Furthermore, the compounds of this invention differ from the compounds of Biggi et al by having a 1-piperazinyl group at position 2 of the 2,4,6-cycloheptatrien-1-one ring.

SUMMARY OF THE INVENTION

The compounds of this invention are represented by formula I

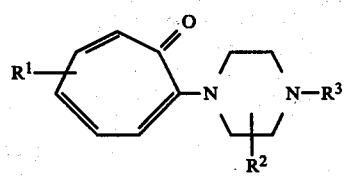

(I)

in which $R^1$ represents a substituent at positions 3, 4, 5, 6 or 7 of the 2,4,6-cycloheptatrien-1-one ring and is selected from hydrogen, halo, lower alkyl, lower alkoxy, trifluoromethyl, or 1-oxo(lower)alkylamino; $R^2$ is hydrogen or lower alkyl having one to three carbon atoms; and $R^3$ is hydrogen, phenyl, lower alkyl, lower alkenyl, lower alkynyl, cyclo(lower)alkyl, lower alkoxycarbonyl, 1-oxo(lower)alkyl, cyclo(lower)alkyl substituted with a lower alkyl; lower alkenyl substituted with phenyl; phenyl mono-, di- or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta[b]furan-2-ylmethyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl or 5-methyl-2,4-imidazolidinedione-5-ylmethyl; or a therapeutically acceptable acid addition salt thereof.

A preferred group of compounds of this invention is represented by formula I in which $R^1$ is hydrogen; $R^2$ is hydrogen or lower alkyl having one to three carbon atoms; and $R^3$ is hydrogen, phenyl, lower alkyl, lower alkenyl, lower alkynyl, cyclo(lower)alkyl, lower alkoxycarbonyl, 1-oxo(lower)alkyl, cyclo(lower)alkyl substituted with a lower alkyl; lower alkenyl substituted with phenyl; phenyl mono-, di- or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta[b]furan-2-ylmethyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl, or 5-methyl-2,4-imidazolidinedione-5-ylmethyl; or a therapeutically acceptable acid addition salt thereof.

A more preferred group of compounds of this invention is represented by formula I in which $R^1$ is hydrogen; $R^2$ is hydrogen or methyl; and $R^3$ is hydrogen, phenyl, lower alkyl, lower alkenyl, lower alkynyl, cyclo(lower)alkyl, lower alkoxycarbonyl, 1-oxo(lower)alkyl, cyclo(lower)alkyl substituted with a lower alkyl; phenyl monosubstituted with lower alkyl, halo or trifluoromethyl; 2-(4,5-dihydro-2-oxazolyl)benzoyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl or 5-methyl-2,4-imidazolidinedione-5-ylmethyl; or a therapeutically acceptable acid addition salt thereof.

A most preferred group of compounds of this invention is represented by formula I in which $R^1$ and $R^2$ are hydrogen; and $R^3$ is hydrogen, lower alkyl, lower alkenyl or lower alkoxycarbonyl; or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to stimulate dopamine receptors in a mammal in need thereof by administering to the mammal an effective dopamine receptor stimulating amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, 1-methylethyl, butyl, 2-methylpropyl, pentyl, hexyl and the like, unless stated otherwise. 1-Methylethyl and 2-methylpropyl also are known as isopropyl and sec-butyl.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "1-oxo(lower)alkyl" or "lower alkanoyl" as used herein means straight chain 1-oxoalkyl radicals containing from two to six carbon atoms and branched chain 1-oxoalkyl radicals containing four to six carbon atoms and includes acetyl, 1-oxopropyl, 2-methyl-1-oxopropyl, 1-oxohexyl and the like.

The term "1-oxo(lower)alkoxy" as used herein means straight chain 1-oxoalkoxy radicals containing from two to six carbon atoms and branched chain 1-oxoalkoxy radicals containing four to six carbon atoms and includes acetyloxy, 1-oxopropoxy, 1-oxobutoxy, 2,2-dimethyl-1-oxopropoxy, 1-oxohexoxy and the like.

The term "lower alkynyl" as used herein means straight chain alkynyl radicals containing from two to six carbon atoms and a branched chain alkynyl radical containing four carbon atoms and includes ethynyl, 2-propynyl, 1-methyl-2-propynyl, 3-hexynyl and the like.

The term "lower alkenyl" as used herein means straight chain alkenyl radicals containing from two to six carbon atoms and branched chain alkenyl radicals containing three or four carbon atoms and includes ethenyl, 2-methyl-2-propenyl, 4-hexenyl and the like.

The term "halo" as used herein means halogens and includes fluorine, chlorine, bromine and iodine, unless stated otherwise.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "cyclo(lower)alkyl substituted with a lower alkyl" as used herein means saturated cyclic hydrocarbon radicals containing from three to six carbon atoms, as defined above, which is substituted with a lower alkyl group and includes 1-methylcyclopropyl, 2-ethylcyclobutyl, 4-propylcyclohexyl and the like.

The term "lower alkanol" as used herein means both straight and branched chain alkanols containing from one to four carbon atoms and includes methanol, ethanol, isopropanol, butanol and the like.

The term "organic proton acceptor" as used herein means the organic bases, or amines for instance, triethylamine, pyridine, N-ethyl-morpholine, 1,5-diazabicyclo[4.3.0]non-5-ene and the like.

The term "inorganic proton acceptor" as used herein means the inorganic bases, preferably the alkali metal hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined herein.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, malic, citric, or tartaric acid; and acids which are sparingly soluble in body fluids and which impart slow-release properties to their respective salts, e.g., pamoic acid, tannic acid or carboxymethyl cellulose.

The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The discovery in the mid-1960's of two major dopamine (DA) systems indicated that this neurotransmitter exerted control over a number of physiological functions. Against this background an interest arose to develop DA receptor agonists to study the function of the dopaminergic systems and to evaluate these agonists as possible therapeutic agents in the Parkinson's disease and certain neuroendocrine disorders, for example, hyperprolactinemia, galactorrhea, amenorrhea, impotence, hypertension and other central nervous system disorders.

The DA receptor agonists exert a variety of pharmacological effects, some of the most characteristic being the ones that occur in animals in which DA deficiency is brought about to mimic the Parkinsonian syndrome. An important model was developed by U. Ungerstedt, Acta. Physiol. Scand., Suppl. 367, 69–93 (1971) who, by means of unilateral injections of 6-hydroxydopamine (6-OHDA) into the DA pathway, could produce selective lesions of the ascending DA pathways on one side of the brain. Ungerstedt (1971) demonstrated in three lesioned rats that DA receptor agonists induced rotational behavior towards the innervated side. The response is due to the development of receptor supersensitivity in the denervated striatum resulting in a higher degree of DA receptor activity on the denervated- as compared to the innervated-side after treatment with DA receptor agonists. Due to this imbalance between the two sides, a rotational behavior is elicited, the direction being always towards the less activated side. It is of interest that in the discovery of the DA receptor stimulating properties of bromocriptine, the 6-OHDA rotational model was utilized [H. Corrodi et al., J. Pharm. Pharmacol., 25, 409–412 (1973)].

In the test for rotational behavior in rats following the unilateral 6-OHDA-induced destruction of one nigrostriatal pathway, the method described by C. J. Pycock and C. D. Marsden, Europ. J. Pharmacol., 47, 167 (1978) was followed. The rats (230–250 g) were anesthetized with sodium pentobarbital (40 mg/kg i.p.) and intracerebral injections were made using a Stoelting stereotaxic instrument, (C. H. Stoelting Co., Chicago, Ill., U.S.A.). Unilateral injections of 6-OHDA hydrobromide (8 $\mu$g/3 $\mu$l delivered at a rate of 1 $\mu$l per min) were made into the ascending median forebrain bundle (MFB) in the lateral hypothalamus according to the coordinates of the De Groot brain atlas, J. De Groot, Verhandel, Koninkl. Ned. Akad. Wetenschap. Natuurk. 52: 1–40 (1959), (A: +4.6, L: ±1.9, V: −2.7). 6-OHDA was made up in ice-cold distilled water containing 0.2 mg/ml ascorbic acid.

Three weeks after operation, the rats were tested for rotational behavior in response to apomorphine hydrochloride (0.25 mg/kg, s.c.). Rats which consistently showed more than 5 turns/min after apomorphine were selected and the compound of formula I was then administered. The rat was immediately placed in the rotometer, described by K. Voith and J. R. Cummings, Can. J. Pharmacol., 54, 551 (1976), and the rotation was continuously recorded until drug effect subsided. By using this test, the compounds of formula I can be shown to be effective dopamine receptor agonists.

A recently developed animal model, described by G. P. Smith and R. C. Young in "Advances in Neurology", Vol. 5, F. H. McDowell and A. Barbeau, Eds., Raven Press, New York, pp. 427–432 (1974), shows that rats exhibit almost complete akinesia in an open field following the bilateral injection of 6-OHDA into the anterolateral hypothalamus. The troponylpiperazines of formula I are able to reverse this 6-OHDA-induced hypokinesia and as a result, function as dopamine receptor agonists. In this test for dopamine receptor agonists, the compounds of formula I exhibit a pharmacological response that is quantitatively comparable to that of apomophine and bromocriptine.

Experiments were performed on male Sprague-Dawley rats housed in air-conditioned quarters. The room was lighted between 0700 and 1900 hr daily and was maintained at a temperature of 24° C.±2° C.

The method of Smith and Young, cited above, was followed. Rats (approximately 280 g) were operated on under sodium pentobarbital anesthesia. Using a Stoelting stereotaxic instrument, the tip of a 26 gauge cannula was positioned in the anterolateral hypothalamus (7 mm anterior to the interaural line, 2 mm lateral to the midline and 8 mm below the dura) according to the De Groot brain atlas, noted above. Via a polyethylene tubing (PE 20) the cannula was connected to a 10 μl syringe which was mounted in a Starrett micrometer head drive, C. H., Stoelting Co., Chicago, Ill. U.S.A. All injections were bilateral. Each injection consisted of 4 μl of distilled water containing 6-OHDA (6.5 μg base/μl) and ascorbic acid (0.4 μg/μl).

The animals had free access to Purina Laboratory Chow pellets and tap water. However since anterolateral hypothalamic 6-OHDA injections produce aphagia and adipsia, intragastric feeding was necessary in order to prevent drastic weight less. The rats received a daily gastric intubation of 2 g of the "modified rat tube feeding diet" (ICN Pharmaceuticals, Inc., Cleveland, Ohio, U.S.A.) mixed with approximately 2 ml tap water.

Ambulation in the open field was evaluated in an apparatus consisting of a wooden box (69 cm×69 cm×42 cm) with an arborite floor. The floor was divided into 36 squares (11.5 cm×11.5 cm). The placement of all four limbs in one square was taken as one ambulation score.

In the present experiments all compounds were evaluated four days after the intracerebral injection of 6-OHDA. The rat was placed into the center of the open field and observed for a 2-min period. Only rats with almost total akinesia were used. Apomorphine, bromocriptine or the compounds of formula I were injected s.c. to groups of 4–12 rats. Subsequently, the number of squares were counted which the animal entered during several 2-min observation periods. Apomorphine was evaluated at 5, 10, 15, 20 and 30 min; bromocriptine at 2, 3, 4, 5, 6 and 7 hr; and the compounds of formula I at 15, 30, 45, 60, 90 and 120 min after injection. Each animal was used only once. The results are expressed as cumulative number of ambulation scores which are the sums of the scores obtained during the 2-min observation periods.

The following substances were used; apomorphine hydrochloride (Macfarlan Smith Ltd., Edinburgh, Scotland), bromocriptine (CB-154) (Sandoz Pharmaceuticals, East Hanover, N.J., U.S.A.) and 6-OHDA hydrobromide (Aldrich Chemical Co., Inc., Milwaukee, Wis., U.S.A.). The compounds were dissolved in distilled water or suspended in distilled water with a few drops of polysorbate 80 (Tween 80; "Tween" is a registered trade mark). If the compound was an oil, 0.4 ml of dimethyl sulfoxide was added. Solutions were prepared fresh on the day of the experiment. The 6-OHDA solution was kept in ice throughout the injection procedure. All doses refer to the base.

Using the above described method, apomorphine at a dose of 0.5 mg/kg exhibited a score of 135±41 and bromocriptine at a dose of 10 mg/kg exhibited a score of 112±23. Similarly, the following representative compounds of formula I are effective dopamine receptor agonists (the amount of the compound and its cumulative ambulation score are indicated in the parentheses): 2-(4-methyl-1-piperazinyl)-2,4,6-cycloheptatrien-1-one (described in Example 1, at a dose of 50 mg/kg exhibited a score of 278±57), 4-(2-oxo-3,5,7-cycloheptatrien-1-yl)-1-piperazine carboxylic acid, ethyl ester (described in Example 1, at a dose of 50 mg/kg exhibited a score of 79±31), 2-[4-(2-propenyl)-1-piperazinyl]-2,4,6-cycloheptatrien-1-one (described in Example 4, at a dose of 50 mg/kg exhibited a score of 155±43), 2-[4-(2-propynyl)-1-piperazinyl]-2,4,6-cycloheptatrien-1-one (described in Example 4, at a dose of 50 mg/kg exhibited a score of 28±6), 2-[4-(1-methylethyl)-1-piperazinyl]-2,4,6-cycloheptatrien-1-one (described in Example 4, at a dose of 50 mg/kg exhibited a score of 431±113), 2-(4-ethyl-1-piperazinyl)-2,4,6-cycloheptatrien-1-one (described in Example 4, at a dose of 50 mg/kg exhibited a score of 70±15), 2-(4-propyl-1-piperazinyl)-2,4,6-cycloheptatrien-1-one (described in Example 4, at a dose of 50 mg/kg exhibited a score of 159±34), and N-[2-[4-(2-oxo-3,5,7-cycloheptatrien-1-yl)-1-piperazinyl]ethyl]acetamide (described in Example 7 at a dose of 50 mg/kg exhibited a score of 36±8).

The above described test method for dopamine receptor agonists shows that the compounds of formula I are active as dopamine receptor agonists. The compounds, thus, can be used clinically in the treatment of hyperprolactinemia, galactorrhoea, amenorrhoea, impotence, diabetes, Parkinsonism, acromegaly, hypertension and other central nervous system disorders which respond to dopamine-receptor stimulation.

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of the formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as dopamine receptor agonists will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, the effective dopamine receptor stimulating amount of the compounds for i.p. administration usually ranges from about 0.1 mg to about 250 mg per kilogram body weight per day in single or divided doses although as aforementioned variations will occur. However a dosage level that is in the range of from about 1.0 to about 100 mg per kilogram body weight per day in single or divided doses is employed most desirably for i.p. administration in order to achieve effective results. For oral administration, effective amounts can range from about 1.0 to about 250 mg per kilogram body weight per day in single or divided doses preferably about 5.0 to 100 mg per kilogram body weight per day.

The compound of formula I, or a therapeutically acceptable salt thereof, also can be used to produce beneficial effects in the treatment of Parkinsonism, hyperprolactinemia and related disorders when combined with a therapeutically effective amount of an agent commonly used in the treatment of Parkinsonism, hyperprolactinemia and related disorders. Such agents include, for example, apomorphine and its derivatives, piribedil and its derivatives, dopaminergic ergot derivatives, especially bromocriptine and lergotrile, 2-amino-6,7-dihydroxy-(1,2,3,4)-tetrahydronaphthalene (ADTN), levodihydroxyphenylalanine (levodopa), combination of levodopa with carbidopa, L-prolyl-L-leucylglycinamide (MIF) and its derivatives, especially L-propyl-N-methyl-D-leucylglycinamide (pareptide), biperiden, cycrimine hydrochloride, procyclidine, trihexyphenidyl hydrochloride, benztropine mesylate, chlorphenoxamine hydrochloride, diphenhydramine hydrochloride, orphenadrine hydrochloride, ethopropazine hydrochloride and the enzymes, monoamine oxidase B and catechol-O-methyl transferase. A combination of the foregoing agents can be substituted for a single agent. Suitable methods of administration, compositions and dosages of the agents are well known in the art; for instance, "Physcan Desk Reference", 32 ed., Medical Economics Co., Oradell, N.J., U.S.A., 1978. When used in combination, the compound of formula I, or its therapeutically acceptable salt, is administered as described previously.

PROCESS

Reaction scheme I illustrates a method for preparing a number of the compounds of formula I.

REACTION SCHEME 1

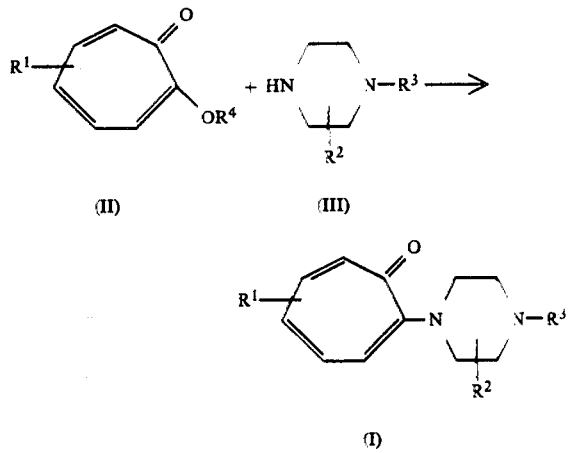

The 2-alkoxy-tropones of formula II suitable as starting materials are described in a number of reports; for example, see the review on tropone derivatives, their preparation and their interconversions by F. Pietra, Chem. Rev., 73, 293 (1973). Thus, the 2-alkoxy-tropones are either known or they can be prepared by conventional means.

Also, the piperazine and piperazine derivatives of formula III are known, commercially available or can be prepared by conventional means. For example, one useful method of preparing a compound of formula III wherein $R^3$ is other than hydrogen, the appropriate nitrogen of the piperazine of formula III wherein $R^2$ is as defined herein and $R^3$ is hydrogen is first protected with an amino protecting group, for instance, benzyl, formyl, tert-butoxycarbonyl and the like. The desired $R^3$ group is then introduced onto the other nitrogen of this protected piperazine; various methods of introducing the $R^3$ group are described hereinafter. Subsequent removal of the protecting group, for example, hydrogenation in the case of benzyl, gives the corresponding piperazine derivative of formula III wherein $R^3$ is other than hydrogen.

With reference to reaction scheme 1, the 2-alkoxy-tropone of formula II in which $R^1$ represents a substituent at positions 3, 4, 5, 6 or 7 of the 2,4,6-cycloheptatrien-1-one ring and is selected from hydrogen, halo, lower alkyl, lower alkoxy, trifluoromethyl or 1-oxo(-lower)alkylamino and $R^4$ is lower alkyl, preferably methyl or ethyl, is condensed with the piperazine derivative of formula III in which $R^2$ is hydrogen or lower alkyl having one to three carbon atoms; and $R^3$ is hydrogen, phenyl, lower alkyl, lower alkenyl, lower alkynyl, cyclo(lower)alkyl, lower alkoxycarbonyl, 1-oxo(-lower)alkyl, cyclo(lower)alkyl substituted with a lower alkyl; lower alkenyl substituted with phenyl; phenyl mono-, di- or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta[b]furan-2-ylmethyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl, or 5-methyl-2,4-imidazolidinedione-5-ylmethyl to obtain the corresponding compound of formula I in which $R^1$, $R^2$, $R^3$ and $R^4$ are as defined herein. The condensation is readily effected by heating a solution of the compound of formula II with one to five, preferably 1.3 to 2.0, molar equivalents of the piperazine of formula III in an inert organic solvent, for example, a lower alkanol, benzene, chloroform, acetonitrile, toluene and the like, preferably methanol or ethanol, at 50° to 100° C. for 10 to 60 hours and isolating the corresponding compound of formula I.

By using the above condensation conditions, condensation of the compound of formula II in which $R^1$ is hydrogen with about one-half molar equivalent of the compound of formula III in which $R^2$ is as defined herein and $R^3$ is hydrogen gives the corresponding compound of formula I in which $R^1$ is hydrogen, $R^2$ is as defined herein and $R^3$ is 1-oxo-2,4,6-cycloheptatrien-2-yl.

The above described condensation of the compounds of formula II and formula III is especially useful for preparing the compounds of formula I in which $R^1$ is hydrogen, $R^2$ is as defined herein and $R^3$ is hydrogen, phenyl, lower alkyl, lower alkoxycarbonyl, 1-oxo-2,4,6-cycloheptatrien-2-yl or phenyl mono-, di- or trisubstituted with lower alkyl, halo or trifluoromethyl.

The above described compounds of formula I in which $R^1$ and $R^2$ are as defined herein and $R^3$ is hydrogen are especially useful for conversion to other compounds of formula I. In one such conversion, the latter compound of formula I in which $R^3$ is hydrogen is condensed in the presence of a proton acceptor with a halide of formula $X-R^3$ wherein X is bromo, chloro or iodo and $R^3$ is lower alkyl, lower alkenyl, lower alkynyl, cyclo(lower)alkyl, lower alkoxycarbonyl, 1-oxo(lower)alkyl, cyclo(lower)alkyl substituted with a lower alkyl; lower alkenyl substituted with phenyl; 2,3-dihydro-8-oxo-cyclohepta[b]furan-2-ylmethyl, 2,3-diacetyloxypropyl, or 2-(1,3-dihydro-1,3-dioxo-2H-isoindol-2-yl)ethyl to obtain the corresponding compound of formula I in which $R^1$ and $R^2$ are as defined herein and $R^3$ is as defined immediately above and 2-(4,5-dihydro-2-oxazolyl)benzoyl. About one to ten, preferably 1.0 to 1.5 molar equivalents of the proton acceptor and about one to five, preferably 1.0 to 1.5, molar equivalents of the halide of formula $X-R^3$ are used. In this condensation, it should be noted that the condensation of the compound of formula I in which $R^3$ is hydrogen with 2-(bromoethyl)-1,3-dihydro-2H-isoindol-1,3-dione gives a separable mixture of the compound of formula I in which $R^1$ and $R^2$ are defined herein and $R^3$ is 2-(4,5-dihydro-2-oxazolyl)benzoyl or 2-(1,3-dihydro-1,3-dioxo-2H-isoindol-2-yl)ethyl. For this condensation, suitable proton acceptors can be selected from organic and inorganic proton acceptors, for example triethylamine, pyridine, N-ethylmorpholine, sodium bicarbonate, sodium or potassium carbonate, sodium or potassium lower alkoxide and the like. Sodium or potassium carbonate is the preferred proton acceptor. Usually the condensation is conducted in an inert organic solvent, for example, benzene, toluene, dichloromethane, chloroform, lower alkanol, acetonitrile, dimethylformide, acetone and the like. Acetonitrile and/or methanol is the preferred solvent for the condensation. To achieve the condensation, the reaction mixture is maintained at 20° to 85° C. for three hours to three days and the compound of formula I is isolated.

The latter conditions are also useful for the condensation of the compound of formula I in which $R^1$ and $R^2$ are as defined herein and $R^3$ is hydrogen with epichlorohydrin to give the corresponding intermediate having the 2,3-dihydroxypropyl group at position 4 of the piperzino ring. Acetylation of this intermediate, in the same manner as described hereinafter, gives the corresponding compound of formula I in which $R^1$ and $R^2$ are as defined herein and $R^3$ is 2,3-diacetyloxypropyl.

Acylation of the compound of formula I in which $R^1$ and $R^2$ are as defined herein and $R^3$ is hydrogen, preferably with about an equivalent of a lower alkanoyl bromide or chloride, or an excess of a lower alkanoic anhydride, in the presence of an organic proton acceptor, preferably benzene or dichloromethane, at 0° to 20° C. for one to ten hours, gives the corresponding compound of formula I in which $R^1$ and $R^2$ are as defined herein and $R^3$ is 1-oxo(lower)alkyl. When this acylation involves acetylation, a preferred method of acetylation is the reaction of the compound of formula I in which $R^3$ is hydrogen with about 5 to 20 molar equivalents of acetic anhydride at 10° to 30° C. for about 10 to 60 minutes to obtain the corresponding compound of formula I in which $R^1$ and $R^2$ are as defined herein and $R^3$ is acetyl.

In another series of reactions, the compound of formula I in which $R^1$ and $R^2$ are as defined herein and $R^3$ is hydrogen is condensed with 1-chloro-2-propanone to obtain the corresponding intermediate having a 2-oxopropyl group at position 4 of the piperazine ring. Reaction of this intermediate with about one molar equivalent of potassium cyanide and about two molar equivalents of ammonium carbonate in a solution of aqueous methanol at about 50° to 70° C. for about 10 to 30 hours gives the corresponding compound of formula I in which $R^1$ and $R^2$ are as defined herein and $R^3$ is 5-methyl-2,4-imidazolidinedione-5-yl-methyl.

In another transformation, the compound of formula I in which $R^1$ and $R^2$ are as defined herein and $R^3$ is 2-(1,3-dihydro-1,3-dioxo-2H-isoindol-2-yl)ethyl is reacted with about one molar equivalent of hydrazine hydrate in ethanol or methanol at about 20° to 30° C. for about 10 to 40 hours to obtain the corresponding intermediate having an 2-aminoethyl group. Acetylation of this intermediate with acetic anhydride, in the same manner as described above, affords the corresponding compound of formula I in which $R^1$ and $R^2$ are as defined herein and $R^3$ is 2-(acetylamino)ethyl.

The following examples illustrate further this invention.

EXAMPLE 1

2-[4-(3-Trifluoromethylphenyl)-1-piperazinyl]-2,4,6-cycloheptatrien-1-one (I: $R^1$ and $R^2$=H and $R^3$=3-trifluoromethylphenyl)

A mixture of 1-(3-trifluoromethylphenyl)-piperazine (2.3 g) and 2-methoxy-2,4,6-cycloheptatrien-1-one (2.0 g) in methanol (50 ml) was refluxed for 24 hr and evaporated. The residue was chromatographed on silica gel (100 g) using ethyl acetate. The eluates were evaporated and crystallized from ethyl acetate-benzene to give the title compound (4.08 g): mp 112°–114° C.; ir (CHCl$_3$) 1570 cm$^{-1}$; uv max (MeOH)350 ($\epsilon$=10575) and 256 nm ($\epsilon$=31730); nmr (CDCl$_3$)$\delta$ 3.5 (m, 8H) and 7.0 (m, 9H); and Anal. Calcd for $C_{18}H_{17}F_3N_2O$: C, 64.66% H, 5.12% N, 8.38% and Found: C, 64.84% H, 5.17% N, 8.54%.

In the same manner, but replacing 1-(3-trifluoromethylphenyl)-piperazine with an equivalent amount of 1-methylpiperazine, 1-(2-methylphenyl)piperazine, 1-(4-chlorophenyl)-3-methylpiperazine, 1-piperazine carboxylic acid ethyl ester, 1-(1,1-dimethylethyl)piperazine, 2 methylpiperazine or 1-phenylpiperazine and when desired, preparing the acid addition salt of the compound of formula I by using the appropriate acid; the following compounds of formula I were obtained respectively: 2-(4-methylpiperazinyl)-2,4,6-cycloheptatrien-1-one(Z)-2-butenedioate (I: $R^1$ and $R^2$=H and $R^3$=Me): mp 118°–120° C. (crystallized from acetone-diethyl ether); ir(CHCl$_3$) 2400, 1705, 1620, 1350 and 1570 cm$^{-1}$; uv max(MeOH) 343 ($\epsilon$=9440) and 250 nm ($\epsilon$=14975); and nmr(CDCl$_3$)$\delta$2.9 (s, 3H), 3.5 (m, 8H), 6.27 (s, 2H), 7.0 (m, 5H) and 14.5 (broad, 2H); 2-[4-(2-methylphenyl)-1-piperazinyl]-2,4,6-cycloheptatrien-1-one (I: $R^1$ and $R^2$=H and $R^3$=2-methylphenyl): mp 115°–116° C. (crystallized from diethyl ether-hexane); ir(CHCl$_3$) 1565 cm$^{-1}$; uv max(MeOH) 353 ($\epsilon$=10000) and 253 nm ($\epsilon$=20095); nmr(CDCl$_3$)$\delta$2.33 (s, 3H), 3.05 (m, 4H), 3.45 (m, 4H) and 6.9 (m, 9H); and Anal. Calcd for C$_{18}$H$_{20}$N$_2$O: C, 77.20% H, 7.14% N, 10.0% and Found: C, 76.97% H, 7.21% N, 9.86%; 2-[4-(4-chlorophenyl)-2-methyl-1-piperazinyl]-2,4,6-cycloheptatrien-1-one (I: $R^1$=H, $R^2$=2-Me and $R^3$=4-chlorophenyl): mp 120°–121° C. (crystallized from diethyl ether-hexane); ir(CHCl$_3$) 1565 cm$^{-1}$; uv max(MeOH)) 352 ($\epsilon$=7250) and 259 nm($\epsilon$=22285); nmr(CDCl$_3$) $\delta$1.13 (d, 3H), 3.5 (m, 7H) and 6.9 (m, 9H); and Anal. Calcd for C$_{18}$H$_{19}$ClN$_2$: C, 68.60% H, 6.08% N, 8.89% and Found: C, 68.61% H, 6.15% N, 8.86%; 4-(2-oxo-3,5,7-cycloheptatrien-1-yl)-1-piperazine carboxylic acid ethyl ester (I: $R^1$ and $R^2$=H and $R^3$=ethoxycarbonyl): mp 95°–98° C. (crystallized from diethyl ether); ir(CHCl$_3$) 1690 and 1570 cm$^{-1}$; uv max(MeOH) 350 ($\epsilon$=9629), 254 ($\epsilon$=13089) and 225 nm ($\epsilon$=12171); nmr(C Cl$_3$) $\delta$1.3 (t, 3H), 3.35 (m, 4H), 3.67 (m, 4H), 4.2 (q, 2H) and 6.9 (m, 5H); and Anal. Calcd for C$_{14}$H$_{18}$N$_2$O$_3$: C, 64.1% H, 6.92% N, 10.68% and Found: C, 64.19% H, 7.03% N, 10.53%; B 2-[4-(1,1-dimethylethyl)-1-piperazinyl]-2,4,6-cycloheptatrien-1-one(Z)-2-butenedioate (I: $R^1$ and $R^2$=H and $R^3$=1,1-dimethylethyl): mp 160°–162° C. (crystallized from diethyl ether-methanol); ir(mull) 2400, 1700 and 1570 cm$^{-1}$; uv max(MeOH) 343 ($\epsilon$=9180) and 250 nm ($\epsilon$=14380); nmr(CDCl$_3$)$\delta$1.45 (s, 9H), 3.50 (m, 8H), 6.20 (s, 2H) and 6.90 (m, 5H); and Anal. Calcd for C$_{15}$H$_{22}$N$_2$O.C$_4$H$_4$O$_4$: C, 62.97% H, 7.23% N, 7.73% and Found: C, 62.56% H, 7.33% N, 7.41%; 2-(3-methyl-1-piperazinyl)-2,4,6-cycloheptatrien-1-one (I: $R^1$ and $R^3$=H and $R^2$=3-Me); and 2-(4-phenyl-1piperazinyl)-2,4,6-cycloheptatrien-1-one; (I: $R^1$ and $R^2$=H and $R^3$=Ph): mp 110°–112° C. (crystallized from ethyl acetate-hexane); ir(CHCl$_3$) 1570 cm$^{-1}$; uv max(MeOH) 350 ($\epsilon$=10280), 254 ($\epsilon$=26020) and 230 nm ($\epsilon$=15445); nmr(CDCl$_3$)$\delta$3.45 (8H) and 7.05 (10H); and Anal. Calcd for C$_{17}$H$_{18}$N$_2$O: C, 76.66% H, 6.81% N, 10.52% and Found: C, 76.54% H, 6.78% N, 10.45%.

Similarly, by condensing 1-methylpiperazine with 7-bromo-2-methoxy-2,4,6-cycloheptatrien-1-one or 5-acetylamino-2-methoxy-2,4,6-cycloheptatrien-1 -one and when desired, preparing the acid addition salt of the compound of formula I by using the appropriate acid, the following compounds of formula I were obtained, respectively: 7-bromo-2-(4-methyl-1-piperazinyl)-2,4,6-cycloheptatrien-1-one methane sulfonate salt (I: $R^1$=7-Br, $R^2$=H and $R^3$=Me): mp 196°–197° C. (crystallized from diethyl ether-methanol); ir(mull) 2600, 1570, 1155 and 1030 cm$^{-1}$; uv max(MeOH) 352 ($\epsilon$=9225) and 270 nm ($\epsilon$=13800); nmr(DMSO-d$_6$)$\delta$2.35 (s, 3H), 2.85 (s, 3H), 3.35 (m, 8H), 7.00 (m, 3H) and 8.15 (m, 1H); and Anal. Calcd for C$_{12}$H$_{15}$BrN$_2$O.CH$_3$SO$_3$H: C, 41.16% H, 5.05% N, 7.39% and Found: C, 41.32% H, 5.01% N, 7.35%; and 5-acetylamino-2-(4-methyl-1-piperazinyl)-2,4,6-cycloheptatrien-1-one (I: $R^1$=5-acetylamino, $R^2$=H and $R^3$=Me): mp 122°–123° C. (crystallized from methanol); ir(CHCl$_3$) 3420, 3280, 1680 and 1540 cm$^{-1}$; uv max(MeOH) 252 nm ($\epsilon$=15230); nmr(CDCl$_3$)$\delta$2.15 (s, 3H), 2.30 (s, 3H), 2.55 (t, 4H), 3.30 (t, 4H), 7.10 (m, 4H) and 8.0 (s, 1H); and Anal. Calcd for C$_{14}$H$_{19}$N$_3$O$_2$: C, 64.34% H, 7.33% N, 16.08% and Found: C, 63.87% H, 7.28% N, 15.96%.

EXAMPLE 2

2,2'-(1,4-Piperazindiyl)-bis-2,4,6-cycloheptatrien-1-one (I: $R^1$ and $R^2$=H and $R^3$=1-oxo-2,4,6-cycloheptatrien-2-yl)

To a solution of piperazine (7.74 g) in methanol (10 ml) at 70° C., a solution of 2-methoxy-2,4,6-cycloheptatrien-1-one (8.16 g) in methanol (50 ml) was added drop by drop. The reaction mixture was heated at 95° C. for 5 hr, cooled and evaporated. The residue was dissolved in chloroform and water. The organic extract was separated, dried and evaporated. The residue was chromatographed on silica gel (250 g) using chloroform then 5% methanol in chloroform, increasing gradually the concentration of methanol up to 20%. The product was recrystallized from methanol to yield 2.9 g of the title compound: mp 184°–186° C.; ir(CHCl$_3$) 1565 cm$^{-1}$; uv max(MeOH) 355 ($\epsilon$=19075), 256 ($\epsilon$=29080) and 223 nm ($\epsilon$=22460); nmr(CDCl$_3$) $\delta$3.55 (m, 8H) and 7.0 (m, 10H); and Anal. Calcd for C$_{18}$H$_{18}$N$_2$O$_2$: C, 73.45% H, 6.16% N, 9.52% and Found: C, 73.76% H, 6.17% N, 9.45%.

EXAMPLE 3

2-(1-Piperazinyl)-2,4,6-cycloheptatrien-1-one (I: $R^1$, $R^2$ and $R^3$=H)

A solution of 2-methoxy-2,4,6-cycloheptatrien-1-one (136 g) and piperazine (136 g) in methanol (250 ml) was refluxed for 4 hr and the reaction vessel was placed in an ice bath. Water (150 ml), then acetic acid was slowly added until the solution was acidic. The mixture was filtered and the filtrate was evaporated and chromatographed on silica gel using chloroform-acetone (1:1) and then with acetic acid-methanol(1:4). The eluates from the latter solvent were evaporated to give an oil of the acetate salt (153 g) of the title compound.

Alternatively, the reaction solution was cooled to induce crystallization of the dimer and filtered. The filtrate was diluted with acetone to 1000 ml and a solution of methane sulfonic acid (106 g) in acetone (250 ml) was added to the filtrate in an ice bath. The precipitate was collected and washed with acetone and diethyl ether to give 146 g of the methane sulfonate salt of the title compound: mp 174°–176° C.; ir(mull) 2900, 1563 and 1180 cm$^{-1}$; uv max(MeOH) 343 ($\epsilon$=8910), 252 ($\epsilon$=13110) and 223 nm($\epsilon$=11250); nmr(DMSO-d$_6$) $\delta$2.35 (s, 3H), 3.35 (m, 8H), 6.95 (m, 5H) and 8.8 (broad, 2H); and Anal. Calcd for C$_{11}$H$_{14}$N$_2$O.CH$_3$SO$_3$H: C, 50.32% H, 6.33% N, 9.80% and Found: C, 50.06% H, 6.39% N, 9.44%.

EXAMPLE 4

2-[4-(2-Propenyl)-1-piperazinyl]-2,4,6-cycloheptatrien-1-one (I: $R^1$ and $R^2$=H, and $R^3$=2-propenyl)

A mixture of 2-(1-piperazinyl)-2,4,6-cycloheptatrien-1-one acetate (15.5 g, described in Example 3), 2-propenyl bromide (7.0 g) and potassium carbonate (13.8 g) in acetonitrile (100 ml) was stirred at room temperature for 16 hr, diluted with water and extracted with chloroform. The chloroform extract was dried and evaporated. The residue (11.0 g) was chromatographed on silica gel (100 g) using chloroform-acetone (1:1) to give 4.7 g of the title compound. The latter material was dissolved in acetone and a solution of maleic acid (2.5 g) in acetone was added. The crystals were collected to obtain 6.4 g of the (Z)-2-butenedioate salt of the title compound: mp 136°–138° C.; ir(CHCl$_3$) 2400, 1900, 1705 and 1570 cm$^{-1}$; uv max(MeOH) 344 ($\epsilon$=11370) and 250 nm ($\epsilon$=17900); nmr(CDCl$_3$) $\delta$3.5 (m, 10H), 5.6 (m, 3H), 6.3 (s, 2H), 7.0 (m, 5H) and 12.4 (s, 2H); and Anal. Calcd for $C_{14}H_{18}N_2O \cdot C_4H_4O_4$: C, 62.42% H, 6.40% N, 8.09% and Found: C, 62.16% H, 6.57% N, 8.31%.

In the same manner but replacing 2-propenyl bromide with an equivalent amount of 2-propynyl bromide, 2-bromopropane, ethyl iodide, 1-bromopropane, 2-bromobutane, bromocyclopentane, bromocyclopropane or 3-chloro-2-methyl-1-propene and when desired, omitting the salt preparation step, the following compounds of formula I were obtained respectively: 2-[4-(2-propynyl)-1-piperazinyl]-2,4,6-cycloheptatrien-1-one-(Z)-butenedioate (I: $R^1$ and $R^2$=H and $R^3$=2-propynyl): mp 145°–146° C. (crystallized from acetone); ir(mull) 3220, 2500 and 1565 cm$^{-1}$; uv max(MeOH) 345 ($\epsilon$=9125) and 252 nm($\epsilon$=14150); nmr(CDCl$_3$)$\delta$2.65 (t, 1H), 3.5 (m, 8H), 3.95 (d, 2H), 6.3 (s, 2H), 6.95 (m, 5H) and 13.2 (s, 2H); and Anal. Calcd for $C_{14}H_{16}N_2O \cdot C_4H_4O_4$: C, 62.78% H, 5.80% N, 8.14% and Found: C, 62.31% H, 6.20% N, 8.37%; 2-[4-(1-methylethyl)-1-piperazinyl)-2,4,6-cycloheptatrien-1-one) (I: $R^1$ and $R^2$=H and $R^3$=1-methyethyl): mp 51.5°–52.5° C. (crystallized from hexane): ir(CHCl$_3$) 1560 cm$^{-1}$; uv max(MeOH) 351 ($\epsilon$=9815), 254 ($\epsilon$=14730) and 222 nm ($\epsilon$=11720); nmr(CDCl$_3$)$\delta$1.05 (d, 6H), 2.65 (m, 5H), 3.35 (t, 4H) and 6.75 (m, 5H); and Anal. Calcd for $C_{14}H_{20}N_2O$: C, 70.37% H, 8.67% N, 12.05% and Found: C, 72.05% H, 8.78% N, 11.74%; 2-(4-ethyl-1-piperazinyl)-2,4,6-cycloheptatrien-1-one (I: $R^1$ and $R^2$=H and $R^3$=Et): ir(CHCl$_3$) 1560 cm$^{-1}$; uv max(MeOH) 350 ($\epsilon$=8760), 255 ($\epsilon$=13135) and 223 nm($\epsilon$=10545); nmr(CDCl$_3$)$\delta$1.10 (t, 3H), 2.45 (q, 2H), 2.60 (t, 4H), 3.35 (t, 4H) and 6.80 (m, 5H); and Anal. Calcd for $C_{13}H_{18}N_2O$: C, 71.52% H, 8.31% N, 12.83% and Found: C, 71.86% H, 8.05% N, 12.48%; 2-(4-propyl-1-piperazinyl)-2,4,6-cycloheptatrien-1-one (I: $R^1$ and $R^2$=H and $R^3$=propyl): ir(CHCl$_3$) 1565 cm$^{-1}$; uv max(MeOH) 351 ($\epsilon$=8780), 255 ($\epsilon$=13180) and 222 nm($\epsilon$=10810); nmr(CDCl$_3$)$\delta$0.9 (t, 3H), 1.55 (m, 2H), 2.40 (m, 2H), 2.65 (t, 4H), 3.35 (t, 4H) and 6.80 (m, 5H); and Anal. Calcd for $C_{14}H_{20}N_2O$: C, 72.37% H, 8.68% N, 12.06% and Found: C, 71.75% H, 8.76% N, 11.95%; 2-[4-(1-methylpropyl)-1-piperazinyl]-2,4,6-cycloheptatrien-1-one (Z)-2-buteneodiate (I: $R^1$ and $R^2$=H and $R^3$=1-methylpropyl): mp 120°–121° C. (crystallized from diethyl ether-methanol); ir(mull) 2500, 1695, 1585, 1564 and 1375 cm$^{-1}$; uv max(MeOH) 343 ($\epsilon$=9240) and 251 nm ($\epsilon$=14425); nmr(DMSO-d$_6$)$\delta$0.9 (t, 3H), 1.23 (d, 3H), 1.6 (m, 2H), 3.35 (m, 9H), 6.0 (s, 2H) and 7.0 (m, 5H); and Anal. Calcd for $C_{15}H_{22}N_2O \cdot C_4H_4O_4$: C, 62.97% H, 7.23% N, 7.73% and Found: C, 62.76% H, 7.18% N, 7.46%; 2-(4-cyclopentyl-1-piperazinyl)-2,4,6-cycloheptatrien-1-one (I: $R^1$ and $R^2$=H and $R^3$=cyclopentyl): mp 102°–103° C. (crystallized from hexane); ir(CHCl$_3$) 16H and 1555 cm$^{-1}$; uv max(MeOH) 350 ($\epsilon$=9720), 254 ($\epsilon$=14370) and 221 nm ($\epsilon$=12200); nmr(CDCl$_3$)$\delta$1.56 (m, 8H), 2.40 (m, 1H), 2.65 (t, 4H), and 6.30–7.30 (m, 5H); and Anal. Calcd for $C_{16}H_{22}N_2O$: C, 74.38% H, 8.58% N, 10.84% and Found: C, 74.60% H, 8.75% N, 10.79%; 2-(4-cyclopropyl-1-piperazinyl)-2,4,6-cycloheptatrien-1-one (I: $R^1$ and $R^2$=H and $R^3$=cyclopropyl); and 2-[4-(2-methyl-2-propenyl)-1-piperazinyl]-2,4,6-cycloheptatrien-1-one (I: $R^1$ and $R^2$=H and $R^3$=2-methyl-2-propenyl): ir(CHCl$_3$) 1560 cm$^{-1}$; uv max(MeOH) 351 ($\epsilon$=10425), 255 ($\epsilon$=16015) and 220 nm($\epsilon$=13640); nmr(CDCl$_3$)$\delta$1.75 (s, 3H), 2.53 (t, 4H), 2.9 (s, 2H), 3.35 (t, 4H), 4.85 (s, 2H) and 6.85 (m, 5H); and Anal. Calcd for $C_{15}H_{20}N_2O$: C, 73.73% H, 8.25% N, 11.47% and Found: C, 73.04% H, 8.26% N, 11.35%.

In the same manner but replacing 2-propenyl bromide with an equivalent amount of 2-(2-bromoethyl)-1,3-dihydro-2H-isoindol-1,3-dione and omitting the salt preparation step, the following two compounds of formula I were obtained, namely; 1,3-dihydro-2-[1-(2-oxo-3,5,7-cycloheptatrien-1-yl)ethyl-2H-isoindol-1,3-dione (I: $R^1$ and $R^2$=H and $R^3$=2-(1,3-dihydro-1,3-dioxo-2H-isoindol-2-yl)ethyl): mp 124°–126° C.; ir(CHCl$_3$) 1770, 1705 and 1560 cm$^{-1}$; uv max(MeOH) 352 ($\epsilon$=8540); 255 ($\epsilon$=13450), 241 ($\epsilon$=18610) and 219 nm($\epsilon$=52770); nmr(CDCl$_3$)$\delta$2.7 (m, 6H), 3.3 (t, 4H), 3.85 (t, 2H), 6.8 (m, 5H) and 7.75 (m, 4H); and Anal. Calcd for $C_{21}H_{21}N_3O_3$: C, 69.41% H, 5.82% N, 11.56% and Found: C, 68.79% H, 5.77% N, 11.30%; and a second product, 2-[4-[2-(4,5-dihydro-2-oxazolyl)benzoyl]-1-piperazinyl]2,4,6-cycloheptatrien-1-one (I: $R^1$ and $R^2$=H and $R^3$=2(4,5-dihydro-2-oxazolyl)benzoyl): mp 195°–196° C.; ir(CHCl$_3$) 1630 and 1565 cm$^{-1}$; uv max(MeOH) 3.50 ($\epsilon$=10140) and 251 nm ($\epsilon$=20715); nmr(CDCl$_3$)$\delta$3.3 (m, 6H), 4.15 (m, 6H) and 7.2 (m, 9H); and Anal. Calcd for $C_{21}H_{21}N_3O_3$: C, 69.41% H, 5.82% N, 11.56% and Found: C, 68.97% H, 5.77% N, 11.22%.

EXAMPLE 5

2-(4-Acetyl-1-piperazinyl)-2,4,6-cycloheptatrien-1-one (I: $R^1$ and $R^2$=H and $R^3$=acetyl)

A solution of 2-(1-piperazinyl)-2,4,6-cycloheptatrien-1-one acetate (8.0 g, described in Example 3) in acetic anhydride (50 ml) was allowed to react at room temperature for 15 min. Methanol (20 ml) was then added, and the solution was evaporated. The residue (7.3 g) was chromatographed on 75 g silica gel with methanol-ethyl acetate (15:85) to yield 5.3 g of purified product. Recrystallization of 4 g from ethyl acetate-hexane afforded 2.9 g of the title compound: mp 64°–66° C.; ir(CHCl$_3$) 3660, 3400, 1635 and 1570 cm$^{-1}$; uv max(MeOH) 350 ($\epsilon$=9920) and 254 nm($\epsilon$=13140); nmr(CDCl$_3$) $\delta$2.10 (s, 3H), 3.30 (m, 4H), 3.70 (m, 4H) and 6.80 (m, 5H); and Anal. Calcd for $C_{13}H_{16}N_2O_2 \cdot 7.01\% H_2O$: C, 62.50% H, 7.23% N, 11.21% and Found: C, 62.21% H, 7.16% N, 11.21%.

EXAMPLE 6

5-Methyl-5-[[4-(2-oxo-3,5,7-cycloheptatrien-1-yl)-1-piperazinyl]methyl]-2,4-imidazolidinedione (I: $R^1$ and $R^2$=H and $R^3$=5-methyl-2,4-imidazolidinedione-5-ylmethyl)

A mixture of 2-(1-piperazinyl)-2,4,6-cycloheptatrien-1-one (12.4 g, described in Example 3), 1-chloro-2-propanone (5.55 g), potassium carbonate (11.04 g) and acetonitrile (120 ml) was refluxed for 4 hr and filtered. Chloroform and water were added to the filtrate. The organic phase was separated, washed with water, dried and evaporated. The residue was chromatographed on silica gel using methanol-ethyl acetate and the eluates were evaporated to give an oil (6.21 g) of 2-[4-(2-oxopropyl)-1-piperazinyl]-2,4,6-cycloheptatrien-1-one: ir(CHCl$_3$) 3660, 3360, 1720, 1710, 1660 nd 1560 cm$^{-1}$; uv max(MeOH) 351 ($\epsilon$=9210), 255 ($\epsilon$=13915) and 221 nm($\epsilon$=11750); nmr(CDCl$_3$) $\delta$2.12 (s, 3H), 2.62 (t, 4H), 3.21 (s, 2H), 3.35 (s, 4H) and 6.40–7.10 (m, 5H); and Anal. Calcd for C$_{14}$H$_{18}$N$_2$O$_2$: C, 68.26% H, 7.37% N, 11.37% and Found: C, 67.83% H, 7.59% N, 11.44%.

To a solution of the latter compound (7.5 g) in methanol (10 ml) heated to 55° C. was added a solution of ammonium carbonate (5.78 g) in 15 ml of water, followed by the addition of potassium cyanide (1.98 g) in 4.5 ml of water. The reaction mixture was maintained at 55° C. for 16 hr, cooled to room temperature and filtered to yield 6.0 g of crude product. Recrystallization from methanol gave 5.4 g of the title compound: mp 231°–232° C.; ir(mull) 3160, 1770, 1710 and 1535 cm$^{-1}$; uv max(MeOH) 353 ($\epsilon$=9600), 255 ($\epsilon$=14520) and 218 nm($\epsilon$=12800); nmr(DMSO-d$_6$) $\delta$1.20 (s, 3H), 2.60 (m, 6H), 3.20 (t, 4H), 6.90 (m, 5H), 7.75 (s, 1H) and 10.40 (s, 1H); and Anal Calcd for C$_{16}$H$_{20}$N$_4$O$_3$: C, 60.74% H, 6.37% N, 17.71% and Found: C, 60.84% H, 6.40% N, 17.59%.

EXAMPLE 7

N-[2-[4-(2-Oxo-3,5,7-cycloheptatrien-1-yl)-1-piperazinyl]ethyl]acetamide (I: $R^1$ and $R^2$=H and $R^3$=2-(acetylamino)ethyl)

To a solution of 1,3-dihydro-2-[4-(2-oxo-3,5,7-cycloheptatrien-1-yl)ethyl]-2H-isoindol-1,3-dione (8.7 g, described in Example 4) in ethanol, hydrazine hydrate (1.305 g) was added and the solution was stirred at room temperature for 24 hr. It was then acidified with 1N hydrochloric acid, left at room temperature for 2 hr and the precipitate was removed by filtration. The filtrate was dissolved in water, made alkaline with diluted sodium hydroxide and extracted with chloroform. The chloroform was evaporated and the residue (6 g) was chromatographed on 100 g silica gel with acetic acid-ethyl acetate (2:8) to yield 4 g of 2-[4-[(2-aminoethyl)-1-piperazinyl]-2,4,6-cycloheptatrien-1-one. A mixture of this compound (4.0 g) and acetic anhydride (40 ml) was allowed to react at room temperature for 48 hr. The acetic anhydride was evaporated at reduced pressure and the residue was chromatographed on 200 g silica gel with methanol to yield 1.6 g of the title compound: mp 117°–118° C.; ir(CHCl$_3$) 3410, 3330, 1665 and 1560 cm$^{-1}$; uv max(MeOH) 356 ($\epsilon$=9780) and 255 nm($\epsilon$=14600); nmr(CDCl$_3$)$\delta$2.0 (s, 3H), 2.6 (m, 6H), 3.35 (m, 6H), 6.0 (broad, 1H) and 6.85 (m, 5H); and Anal. Calcd for C$_{15}$H$_{21}$N$_3$O$_2$: C, 65.43% H, 7.69% N, 15.26% and Found: C, 65.09% H, 7.67% N, 5.11%.

EXAMPLE 8

2-[4-(2,3-Diacetyloxypropyl)-1-piperazinyl]-2,4,6-cycloheptatrien-1-one (I: $R^1$ and $R^2$=H and $R^3$=2,3-diacetyloxypropyl)

A mixture of 2-(1-piperazinyl)-2,4,6-cycloheptatrien-1-one acetate (12.4 g, described in Example 3), epichlorohydrin (5.55 g), potassium carbonate (11.04 g) and acetonitrile (120 ml) was refluxed for 48 hr and filtered. The filtrate was evaporated and the residue (9 g) was chromatographed twice on silica gel with methanol-ethyl acetate (1:9) to yield 2.92 of a mixture of 2-[4-(2,3-dihydroxypropyl)-1-piperazinyl-2,4,6-cycloheptatrien-1-one and 1,3-bis[4-(2-oxo-3,5,7-cycloheptatrien-1-yl)-piperazinyl]-2-propanol.

A solution of this mixture (2.8 g) in pyridine (20 ml) and acetic anhydride (20 ml) was stirred at room temperature for 24 hr and evaporated. The residue was dissolved in ethyl acetate, and the solution was washed with 1N sodium hydroxide, then with water, dried over magnesium sulfur and evaporated. The residue (1.9 g) was chromatographed on 100 g silica gel first with ethyl acetate to give the title compound (0.66 g): ir(CHCl$_3$) 1730, 1612, 1560 and 1250 cm$^{-1}$; uv max(MeOH) 357 ($\epsilon$=4520) and 255 nm($\epsilon$=6750); nmr(CDCl$_3$)$\delta$2.08 (s, 6H), 2.55 (d, 2H), 2.65 (m, 4H), 3.25 (m, 4H), 4.09 and 4.36 (2d, 2H), 5.20 (m, 1H) and 6.68–6.99 (m, 5H); and Anal. Calcd for C$_{18}$H$_{24}$N$_2$O$_5$: C, 62.05% H, 6.94% N, 8.04% and Found: C, 61.99% H, 7.10% N, 7.70%. The above silica gel column was then eluted with acetone. The eluates were evaporated to give a residue (1.2 g) which was crystallized from diethyl ether-ethyl acetate to give 0.35 g of 1,3-bis[4-(2-oxo-3,5,7-cycloheptatrien-1-yl)-1-piperazinyl]-2-propanol acetate: mp 104°–106° C.; ir(CHCl$_3$) 1724, 1612 and 1555 cm$^{-1}$; uv max(MeOH) 358 ($\epsilon$=19380), 255 ($\epsilon$=29100) and 220 nm($\epsilon$=23020); nmr(CDCl$_3$)$\delta$2.06 (s, 3H), 2.55 (d, 4H), 2.65 (t, 8H), 3.33 (t, 8H), 5.20 (m, 1H) and 6.50–7.30 (m, 10H); and Anal. Calcd for C$_{27}$H$_{34}$N$_4$O$_4$: C, 67.76% H, 7.16% N, 11.71% and Found: C, 67.45% H, 7.10% N, 11.44%.

We claim:

1. A compound of the formula

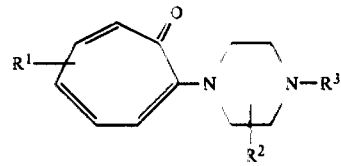

in which $R^1$ represents a substituent at positions 3, 4, 5, 6 or 7 of the 2,4,6-cycloheptatrien-1-one ring and is selected from hydrogen, halo, lower alkyl, lower alkoxy, trifluoromethyl, or 1-oxo(lower)alkylamino; $R^2$ is hydrogen or lower alkyl having one to three carbon atoms; and $R^3$ is hydrogen, phenyl, lower alkyl, lower alkenyl, lower alkynyl, cyclo(lower)alkyl, lower alkoxycarbonyl, 1-oxo(lower)alkyl, cyclo(lower)alkyl substituted with a lower alkyl; lower alkenyl substituted with phenyl; phenyl mono-, di or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta[b] furan-2-ylmethyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl or 5-methyl-2,4-imidazolidinedione-5-ylmethyl; or a therapeutically acceptable acid solution salt thereof.

2. A compound of claim 1 in which $R^1$ is hydrogen; $R^2$ is hydrogen or lower alkyl having one to three carbon atoms; and $R^3$ is hydrogen, phenyl, lower alkyl, lower alkenyl, lower alkynyl, cyclo(lower)alkyl, alkoxycarbonyl, 1-oxo(lower)alkyl, cyclo(lower)alkyl substituted with a lower alkyl; lower alkenyl substituted with phenyl; phenyl mono-, di- or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta furan-2-ylmethyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl, or 5-methyl-2,4-imidazolidinedione-5-ylmethyl; or a therapeutically acceptable acid addition salt thereof.

3. A compound of claim 1 in which $R^1$ is hydrogen; $R^2$ is hydrogen or methyl; and $R^3$ is hydrogen, phenyl, lower alkyl, lower alkenyl, lower alkynyl, cyclo(lower)alkyl, lower alkoxycarbonyl, 1-oxo(lower)alkyl, cyclo(lower)alkyl substituted with a lower alkyl; phenyl monosubstituted with lower alkyl, halo or trifluoromethyl; 2-(4,5-dihydro-2-oxazolyl)benzoyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl or 5-methyl-2,4-imidazolidinedione-5-ylmethyl; or a therapeutically acceptable acid addition salt thereof.

4. A compound of claim 1 in which $R^1$ and $R^2$ are hydrogen; and $R^3$ Is hydrogen, lower alkyl, lower alkenyl or lower alkoxycarbonyl; or a therapeutically acceptable acid addition thereof.

5. 2-(4-Methyl-1-piperazinyl)-2,4,6-cycloheptatrien-1-one, a compound of claim 1 wherein $R^1$ and $R^2$ are hydrogen and $R^3$ is methyl.

6. 2-[4-(2-Methylphenyl)-1-piperazinyl]-2,4,6-cycloheptatrien-1-one, a compound of claim 1 wherein $R^1$ and $R^2$ are hydrogen and $R^3$ is 2-methylphenyl.

7. 2-[4-(4-Chlorophenyl)-2-methyl-1-piperazinyl]-2,4,6-cycloheptatrien-1-one, a compound of claim 1 wherein $R^1$ is hydrogen, $R^2$ is 2-methy and $R^3$ is 4-chlorophenyl.

8. 4-(2-Oxo-3,5,7-cycloheptatrien-1-yl)-1-piperazine carboxylic acid ethyl ester, a compound of claim 1 wherein $R^1$ and $R^2$ are hydrogen and $R^3$ is ethoxycarbonyl.

9. 2,2'-(1,4-Piperazinidyl)-bis-2,4,6-cycloheptatrien-1-one, a compound of claim 1 wherein $R^1$ and $R^2$ are hydrogen and $R^3$ is 1-oxo-2,4,6-cycloheptatrien-2-yl.

10. 2-(1-Piperazinyl)-2,4,6-cycloheptatrien-1-one, a compound of claim 1 wherein $R^1$, $R^2$ and $R^3$ are hydrogen.

11. 2-[4-(2-Propenyl)-1-piperazinyl]-2,4,6-cycloheptatrien-1-one, a compound of claim 1 wherein $R^1$ and $R^2$ are hydrogen and $R^3$ is 2-proponyl.

12. 1,3-Dihydro-2-[4-(2-oxo-3,5,7-cycloheptatrien-1-yl)ethyl]-2H-isoindol-1,3-dione, a compound of claim 1 wherein $R^1$ and $R^2$ are hydrogen and $R^3$ is 2-(1,3-dihydro-1,3-dioxo-2H-isoindol-2-yl)ethyl.

13. 2-[4-[2-(4,5-Dihydro-2-oxazolyl)benzoyl]-1-piperazinyl]-2,4,6-cycloheptatrien-1-one, a compound of claim 1 wherein $R^1$ and $R^2$ are hydrogen and $R^3$ is 2-(4,5-dihydro-2-oxazolyl)benzoyl.

14. 2-[4-(2-Propynyl)-1-piperazinyl]-2,4,6-cycloheptatrien-1-one, a compound of claim 1 wherein $R^1$ and $R^2$ are hydrogen and $R^3$ is 2-propynyl.

15. 2-[4-(1,1-Dimethylethyl)-1-piperazinyl]-2,4,6-cycloheptatrien-1-one, a compound of claim 1 wherein $R^1$ and $R^2$ are hydrogen and $R^3$ is 1,1-dimethylethyl.

16. 7-Bromo-2-(4-methyl-1-piperazinyl)-2,4,6-cycloheptatrien-1-one, a compound of claim 1 wherein $R^1$ is 7-bromo, $R^2$ is hydrogen and $R^3$ is methyl.

17. 5-Acetylamino-2-(4-methyl-1-piperazinyl)-2,4,6-cycloheptatrien-1-one, a compound of claim 1 wherein $R^1$ is 5-acetylamino, $R^2$ is hydrogen and $R^3$ is methyl.

18. 2-[4-(1-Methylethyl)-1-piperazinyl]-2,4,6-cycloheptatrien-1-one, a compound of claim 1 wherein $R^1$ and $R^2$ are hydrogen and $R^3$ is 1-methylethyl.

19. 2-(4-Ethyl-1-piperazinyl)-2,4,6-cycloheptatrien-1-one, a compound of claim 1 wherein $R^1$ and $R^2$ are hydrogen and $R^3$ is ethyl.

20. 2-(4-Propyl-1-piperazinyl)-2,4,6-cycloheptatrien-1-one, a compound of claim 1 wherein $R^1$ and $R^2$ are hydrogen and $R^3$ is propyl.

21. 2-[4-(1-Methylpropyl)-1-piperazinyl]-2,4,6-cycloheptatrien-1-one, a compound of claim 1 wherein $R^1$ and $R^2$ are hydrogen and $R^3$ is 1-methylpropyl.

22. 2-(2-Cyclopentyl-1-piperazinyl)-2,4,6-cycloheptatrien-1-one, a compound of claim 1 wherein $R^1$ and $R^2$ are hydrogen and $R^3$ is cyclopentyl.

23. 2-(4-Acetyl-1-piperazinyl)-2,4,6-cycloheptatrien-4-one, a compound of claim 1 wherein $R^1$ and $R^2$ are hydrogen and $R^3$ is acetyl.

24. 5-Methyl-5-[[4-(2-oxo-3,5,7-cycloheptatrien-1-yl)-1-piperazinyl]methyl]-2,4-imidazolidinedione, a compound of claim 1 wherein $R^1$ and $R^2$ are hydrogen and $R^3$ is 5-methyl-2,4-imidazolinedione-5-ylmethyl.

25. N-[2-[4-(2-Oxo-3,5,7-cycloheptatrien-1-yl)-1-piperazinyl]ethyl]acetamide, a compound of claim 1 wherein $R^1$ and $R^2$ are hydrogen and $R^3$ is 2-(acetylamino)ethyl.

26. 2-[4-(2,3-Diacetyloxypropyl)-1-piperazinyl]-2,4,6-cycloheptatrien-1-one, a compound of claim 1 wherein $R^1$ and $R^2$ are hydrogen and $R^3$ is 2,3-diacetyloxypropyl.

27. 2-(4-Phenyl-1-piperazinyl)-2,4,6-cycloheptatrien-1-one, a compound of claim 1 wherein $R^1$ and $R^2$ are hydrogen and $R^3$ is phenyl.

28. 2-(4-Cyclopropyl-1-piperazinyl)-2,4,6-cycloheptatrien-1-one, a compound of claim 1 wherein $R^1$ and $R^2$ are hydrogen and $R^3$ is cyclopropyl.

29. 2-[4-(2-Methyl-2-propenyl)-1-piperazinyl]-2,4,6-cycloheptatrien-1one, a compound of claim 1 wherein $R^1$ and $R^2$ are hydrogen and $R^3$ is 2-methyl-2-propenyl.

30. 2-[4-(3-Trifluoromethylphenyl)-1-piperazinyl]-2,4,6-cycloheptatrien-1one, a compound of claim 1 wherein $R^1$ and $R^2$ are hydrogen and $R^3$ is 3-trifluoromethylphenyl.

31. A pharmaceutical composition, for stimulating dopamine receptors in a mammal in need thereof, which comprises an effective dopamine receptor stimulating amount of a compound of the formula

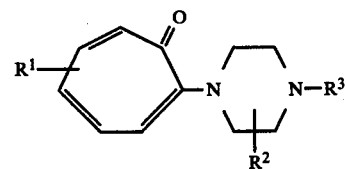

in which $R^1$ represents a substituent at positions 3, 4, 5, 6 or 7 of the 2,4,6-cycloheptatrien-1-one ring and is selected from hydrogen, halo, lower alkyl, lower alkoxy, trifluoromethyl, or 1-oxo(lower)alkylamino; $R^2$ is hydrogen or lower alkyl having one to three carbon atoms; and $R^3$ is hydrogen, phenyl, lower alkyl, lower alkenyl, lower alkynyl, cyclo(lower)alkyl, lower alkoxycarbonyl, 1-oxo(lower)-alkyl, cyclo(lower)alkyl substituted with a lower alkyl; lower alkenyl substituted with phenyl; phenyl mono-, di- or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta[b]furan-2-ylmethyl, oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl or 5-methyl-2,4-imidazolidinedione-5-ylmethyl; or a therapeutically acceptable acid addition salt thereof, and a pharmaceutically acceptable carrier therefor.

32. A method of stimulating dopamine receptors in a mammal in need thereof, which comprises administering to said mammal an effective dopamine receptor stimulating amount of a composition of claim 31.

33. A method of stimulating dopamine receptors in a mammal in need thereof, which comprises administering to said mammal an effective dopamine receptor stimulating amount of a composition of claim 31, in combination with an effective amount of an agent selected from bromocriptine, lergotrile, levodopa, combination of levodopa and carbidopa, L-prolyl-L-leucylglycinamide and L-prolyl-N-methyl-D-leucylglycinamide.

34. The method of claim 33 wherein the composition of claim 31, and said agent are administered sequentially or simultaneously.

35. A pharmaceutical composition for stimulating dopamine receptors in a mammal in need thereof comprising an effective dopamine receptor stimulating amount of a compound of the formula

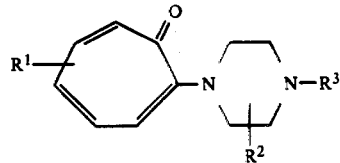

in which $R^1$ represents a substituent at positions 3, 4, 5, 6 or 7 of the 2,4,6-cycloheptatrien-1-one ring and is selected from hydrogen, halo, lower alkyl, lower alkoxy, trifluoromethyl, or 1-oxo(lower)alkylamino; $R^2$ is hydrogen or lower alkyl having one to three carbon atoms; and $R^3$ is hydrogen, phenyl, lower alkyl, lower alkenyl, lower alkynyl, cyclo(lower)alkyl, lower alkoxycarbonyl, 1-oxo(lower)alkyl, cyclo(lower)alkyl substituted with a lower alkyl; lower alkenyl substituted with phenyl; phenyl mono-, di- or trisubstituted with lower alkyl, halo, lower alkoxy, hydroxy or trifluoromethyl; 2-(4,5-dihydro-2-oxazolyl)benzoyl, 2,3-dihydro-8-oxo-cyclohepta[b]furan-2-ylmethyl, 1-oxo-2,4,6-cycloheptatrien-2-yl, 2-(acetylamino)ethyl, 2,3-diacetyloxypropyl, 2-(1,3-dihydro-1,3-dioxo-2H-isoindol-2-yl)ethyl or 5-methyl-2,4-imidazolidinedione-5-ylmethyl; or a therapeutically acceptable acid addition salt thereof, and an agent selected from bromocriptine, lergotrile, levodopa, combination of levodopa and carbidopa, L-prolyl-L-leucylglycinamide and L-prolyl-N-methyl-D-leucylglycinamide.

* * * * *